United States Patent
Edebo

(10) Patent No.: US 6,627,430 B2
(45) Date of Patent: Sep. 30, 2003

(54) CULTIVATION OF ZYGOMYCETES FROM SPENT SULFITE LIQUOR

(76) Inventor: Lars Edebo, S-412 70, Göteborg (SE)

(*) Notice: Subject to any disclaimer, the term of this patent is extended or adjusted under 35 U.S.C. 154(b) by 107 days.

(21) Appl. No.: 09/977,428

(22) Filed: Oct. 15, 2001

(65) Prior Publication Data

US 2002/0025571 A1 Feb. 28, 2002

Related U.S. Application Data

(63) Continuation of application No. PCT/SE00/00729, filed on Apr. 14, 2000.

(30) Foreign Application Priority Data

Apr. 16, 1999 (SE) .............................................. 9901351

(51) Int. Cl.[7] .................................................. C12N 1/24
(52) U.S. Cl. ........................ 435/276; 435/277; 435/278; 424/769
(58) Field of Search ................................ 435/276, 277, 435/278; 424/769

(56) References Cited

FOREIGN PATENT DOCUMENTS

| JP | 06105677 A | 4/1994 |
|---|---|---|
| SE | 8903368-2 | 10/1971 |
| WO | WO 99/00512 | 1/1999 |

OTHER PUBLICATIONS

"Decolorization and Detoxification of Extraction–Stage Effluent from Chlorine Bleaching of Kraft Pulp by Phizopus oryzae", Nagatathnamma et al., Applied and Environmental Microbiology, Mar., 1999, vol. 65, No. 3, pp.: 1078–1082.

Growth of Scytalidium Acidophilum On Defined Media, Whey and Acid Sulphite Waste:, Miller et al., Chemistry and Biology Research Institute, CIP Research Ltd., Hawkesbury, Ontario, Canada, International Biodeterioration, 1984, vol. 20, No. 1, pp.: 27–31.

"Conversion of Spent Sulphite Liquor Sugars to Fumaric Acid by Rhizopus Species", Romano et al., U.S. Department of Health, Education, and Welfare, Cincinnati, Ohio, pp.: 710–723.

"Production of fodder proteins from spent sulfite liquors by aspergillus and rhizopus fungi", Celuloza Hirtie 19, No. 4: 146–53, Apr., 1970, Dialog Information Services, File 240, Paperchem, Dialog accession No. 00049960.

"Culturing Basidiomycetes e.g. shiitake or hiratake–in presence of lignin sulphonate, giving improved colour and texture" File WPI, Derwent accession No. 1984–179651, Biotec KK.

"Production of Organic Acids From Hydrolyzate Media", Berezina G.O. et al, SSR Biol. No. 4: 1967, Dialog Information Services, file 240, Dialog accession No. 00010120, Paperchem No. AB3900367.

"Decolorization and Detoxification fo Extraction–Stage Effluent from Chlorine Bleaching of Kraft Pulp by Rhizopus Oryzae", Applied and Environmental Microbiology, vol. 65, No. 3, Mar. 1999, R. Nagarathnamma et al.

*Primary Examiner*—Jean C. Witz
(74) *Attorney, Agent, or Firm*—Samuels, Gauthier & Stevens, LLP

(57) ABSTRACT

The present invention relates to a process for the cultivation of chitin/chirosanrich, filamentous fungi with capacity to assimilate mannose as well as xylose, galactose, and glucose, wherein the cultivation of the filamentous fungi in a liquid medium extracted from wood in the production of paper whereupon the said filamentous fungi are recovered from the medium.

25 Claims, No Drawings

CULTIVATION OF ZYGOMYCETES FROM SPENT SULFITE LIQUOR

This is a continuation of copending application(s) International Application PCT/SE00/00729 filed on Apr. 14, 2000 and which designated the U.S.

TECHNICAL FIELD

The present invention relates to a process for the cultivation of chitin/chitosanrich, filamentous fungi with capacity to assimilate mannose as well as xylose, galactose, and glucose for a further manufacture of a porous structure comprising cell walls having good absorption ability, as well as a black liquor freed from sugars.

BACKGROUND

In traditional biotechnology the aim has been to use an organism to produce one product of commercial value. This might be a substance with high biological activity and value such as an antibiotic or a hormone. Also less valuable material such as single cell protein and single cell oil are produced. The higher the value of the product the less is the importance of the cost of media and recovery of by-products. When the commercial value of the product is low, the economy of the process is improved by development of a system consisting of a low-cost substrate, a non-expensive production process and the use of several products from the process both such that are produced by the biosynthesis and such that remain in the medium used for cultivation, since the cultivation process might have removed undesired components from the cultivation medium.

In the preparation process for piper pulp from wood in the sulfite process ca half of the wood is extracted in the sulfite liquor as lignosulfonate 60%, sugars 20%, and other material 20%. The dominating sugars are mannose, xylose, galactose, and glucose. Xylose in a pentose, the others are hexoses. The hexoses are readily fermented by yeast, Saccharomyces cerevisiae, into ethanol, whereas the pentoses are not fermented unless the yeast is genetically modified. Xylose it particularly abundant in hardwood. Furthermore the removal of the yeast by centrifugation and the recovery of ethanol by distillation are expensive processes, such that the economy of the entire process has narrow margins.

Lignosulfonate may be concentrated by evaporation and used for binding in animal feed and concrete. In animal feed part of the sugar may be used as a nutrient by the animal being fed, however, the concentration of sugars to be used is fairly low.

When lignosulfonate is used for binding and dispersion in concrete the presence of sugars will delay hardening. Thus different procedures are being developed in order to remove the sugars.

Moulds in contrast to yeasts grow as filaments, and may be harvested from liquid media by simple sieving. Zygomycetes moulds are known to grow well on moist wood causing respiratory allergy in law-mill workers.

Certain zygomycetes species, particularly *Rhizopus oligosporus* and *R. oryzae* have been used since long for food preparation in south-east Asia especially tempeh which is like a camembert made from soy furthermore zygomycetes are used for the production of a great number of different extracellular and intracellular enzymes. One taxonomic characteristic of zygomycetes is that the hyphae (filaments) are lacking septa which make them into microscopical tubes. Another characteristic is that their cell walls contain very high concentrations of chitin/chitosan in a net-work like a micro-sponge. It has previously been found that these cell walls have very good binding properties for several kinds of biological material being negatively charged (EP 0 494 950 B1) as well as for water (Swedish patent application 9801373-3); the material has also antimicrobial effect. The water binding capacity is in the same range as polyacrylate super-absorbents. The polyacrylates are petrochemical products which are difficult to decompose by composting, whereas the cell wall material is made from renewable sources and is readily decomposed in the environment. As a consequence the cell wall material is being exploited for hygienic and infection-preventive purposes (Swedish patent Application 9801373-3).

Thus there is a need for a process which can transfer the drawbacks of the present sulfite liquor because it is an environmental problem, when it is discarded into the environment as such and it is not optimal for use of the lignosulfonate because of the presence of sugar.

The present invention exploits the growth of zygomycetes with the consumption of sugars. The zygomycetes growth will primarily be used for the preparation of cell wall material. However, the very use of an edible mould will eventually make a number of products useful as well as a number of metabolites, e g lactic acid might be recovered.

SUMMARY OF THE PRESENT INVENTION

The present invention concerns a procedure for cultivation of zygomycetes for the production of a material consisting of a porous structure of cell walls with high capacity to absorb and transport liquid, particularly water, and good binding power for biomacromolecules and cells including micro-organisms. In this process the sulfite liquor from the paper pulp industry is cleared from its sugar content.

An extraction process is employed which removes the cell content (protoplasm) and opens tip the cell walls, such that a microporous net-work is formed; alternatively a large number of finely dispersed filaments may surround the former cell wall. The fungal cell walls mainly exist as microtubes (capillaries), and the large number of microtubes gives the material a filamentous appearance.

The porous cell wall material is obtained from a fungus e g belonging to the division Zygomycota and contains a high proportion of hexosamine. The fungal cell material may be disintegrated and is extracted with chemicals such that a suspension is formed. Alternatively the cell material is extracted directly. The suspension is then dried in such a way that the resulting material gets a porous structure e g by air-drying, spray-drying, or preferably by freeze-drying. The resulting material gets a unique capillary system which is capable of absorbing and transporting large volumes of liquid. It can also adsorb proteins and other macromolecules, and cells as bacteria and yeasts. In this context porous implies that the material contains large quantities of air. Thus it has a low density, 0.1 g/cm$^3$, preferably 0.05 g/cm$^3$ at the most. Since the binding capacity of the material is very much dependent of an acid pH, it is of great importance that the counter-ion (anion) is non-volatile. One very useful anion is lactate, since it is non-volatile and has been used widely in skin applications. It is even produced by Rhizopus under the present conditions.

After freeze-drying the material contains a large proportion of air which can be replaced by liquid, macromolecules, and cells e g microorganisms. Consequently the porous fungal cell-wall structure may be used as an absorbent for liquid as well as molecules, particles and cells. After absorption of water the material retains its original form as set before freeze-drying and does not show any sign of disintegration, neither after a long time (>1 week). Due to the fine capillary system of the material, it has a good capacity to spread the liquid without the addition of other fibres.

The material can be dried as it is or bound to another surface. This surface may be a foam, a film or a fibre e g cellulose or synthetic fibre. If the fibre is absorbing, mainly liquid absorbing capacity is obtained. If the fibre is made from plastics, the capacity to adsorb macromolecules and microorganisms is more conspicuous. The material can also be fastened to a surface after drying. It can also be adsorbed to a surface after disintegration of the cell wall filaments as by freeze-pressing.

Furthermore the material may be doped with polar or negatively charged macromolecules such as certain proteins and polysaccharides. New properties are added to the material with the doping. When the material is doped with an enzyme, the material acquires enzymatic activity.

DETAILED DESCRIPTION OF THE PRESENT INVENTION

In order to find zygomycetes strains with good capacity to use the sugars present in sulfite liquor 30 strains representing 10 species were tested with respect to assimilation of 10 different sugars including mannose, xylose, galactose, and glucose. The results clearly showed that there were great differences between the species and also between strains belonging to the same species with respect to growth from the different sugars. It was also obvious that certain sugars such as glucose and mannose were assimilated by a large number of zygomycetes strains, whereas other sugars were less readily assimilated. Of particular interest in this connection was that xylose, which is a pentose and not fermented by the common yeasts used for ethanol production, could be assimilated by a few zygomycetes strains, also by those belonging to edible species. One particularly useful strain is *Rhizopus oryzae* CCUG 28958.

When *Rhizopus oryzae* CCUG 28958 and a few more strains were inoculated into sulfite liquor from different paper mills provided with a nitrogen source and a phosphate source, it was found that the property to supply growth of the zygomycetes strains differed considerably between different liquids. Furthermore, neither concentrated sulfite liquor (dry wt 50%) nor fresh sulfite liquor (dry wt 10%) supplied growth, but when concentrated sulfite liquor was diluted with four times its volume of water (dry wt 10%), very good growth occurred indicating that fresh sulfite liquor contained antifungal substances and the osmotic effect of concentrated liquor was inhibitory.

Thus it has been possible to cultivate edible, chitin/chitosan-rich filamentous moulds in sulfite liquor with surprisingly high yield. So far nearly all hexoses (ca 98%) in the sulfite liquor have been consumed, most of the xylose (ca 80%), whereas arabinose, which was the smallest portion to start with, was seemingly unaffected.

Thus the present invention produces at lest two valuable results by the cultivation of edible fungal mycelium on sulfite liquor which may be an environmentally disturbing by-product from the production of paper pulp. Since sulfite liquor has been used in minor quantities for binding of feed consumed by animals used for human food "the entire process seems to be free of toxic compounds and might be used for food and other applications related to the human and animal body.

1. The cultivation results in the removal of sugars, primarily mannose, xylose, galactose, and glucose from the sulfite liquor, such that the value of the remaining lignosulfonate" which seems unaffected with respect to molecular weight etc.—as fluidizer and binder in concrete is increased.
2. Concurrently the cultivation produces mycelium which can be used as source of cell wall material with absorbing properties as above. Other cell components such as e g enzymes and omega-3 fat acids can be recovered. Since edible fungal species are cultivated in a non-toxic medium, several components with nutrient, pharmacological and catalytic properties might be recovered and used in close connection to the human body. Further metabolites as e g lactic acid might be released into the medium and recovered easily e g as insoluble Ca-lactate.

Porous cell-wall material with high absorbing capacity for water, proteins, cells, and other negatively charged compounds are rich in chitosan/chitin which are polymers of glucosamine and N-acetylglucosamine. Moulds belonging to the division Zygomycota with the genera Absidia, Mucor and Rhizopus have been used. After the cultivation the fungal mycelium is extracted in order to remove lipids, proteins, nucleic acids and soluble chitosan. The mycelium might be disintegrated e g by freeze-pressing in order to facilitate the extraction. Organic solvents e g hot ethanol might be used for extraction of lipids. Hot alkaline liquids as sodium hydroxide might be used to extract proteins and nucleic acids this extraction might be facilitated by using hydrolysing enzymes. Soluble chitosan might be extracted with acids such as acetic acid.

It is also possible to perform the extraction of the mycelium directly starting with alkaline liquids at elevated temperatures followed by acids. Then a suspension of cell-wall material is obtained. Methods for the production of the suspension is described in the Swedish patent SE-C-465678 and the Swedish patent application 9801373-3. This method is only an example, and the invention is not limited to structures produced by this method.

The suspension is dried in such a way that the material gets a porous structure e g by air-drying or spray-drying but preferably by freeze-drying. When the material is allowed to dry in air, usually a less porous structure is obtained such that the material loses its lightness.

The drying conditions can be improved by mixing certain additives into the suspension. An alcohol e g isopropanol can be added, which leads to drying by solvent exchange. A surface active agent e g Triton X-100 can be added to reduce the surface tension of the suspension. The material is usually used at acid pH levels, preferably pH 3–5 in order to promote the protonation of the cell-wall material, and further compounds may be added in order to affect the charge and polarity of the material. The stability of the material in the ambient air is promoted if a non-volatile anion e g lactate is used rather than the volatile acetate as counter-ion in the positively charged cell-wall material.

Also macromolecules such as proteins e g enzymes or charged polysaccharides such as heparin may be added to the suspension. Then new properties are given to the material in relation to what has been added.

If e g enzyme is added, material with enzymatic activity is obtained. The resulting material, especially after freeze-drying, obtains a unique capillary system which can absorb and transport large quantities of liquid. Because of its porous structure it has a low density, which is at most 0.1 g/cm$^3$, preferably 0.05 g/cm$^3$. Consequently, the material contains large volumes of air which may be exchanged for liquid or biological material. Therefore the porous fungal cell-wall structure is an excellent absorbent. The structure can handle free swelling, whereby the material retains its 3-dimensional shape after free swelling in water and does not show any signs of disintegration/dissolution even after a long time (>1 week). Due to the fine capillary system of the structure it has also capacity to spread the liquid, without the need of additional fibres. The material absorbs at least 15 ml/g of 1% NaCl.

The material can transport large volumes of liquid rapidly which occurs in a material which largely consists of air. The empty volume is at least 80%, preferably at least 90%, and more preferably 95%.

Usually such low-density materials are characterised by high absorption capacity at active addition of liquid but poor capacity for transport and spreading. In the fungal cell wall material there is a network of interconnected cell wall tubes which form a continuous system of fine capillary pores which accomplish the high soaking capacity. In combination with the large empty volume which is accessible for the arriving liquid, this creates a conspicuous capacity for rapid and voluminous liquid transport. The water transporting capacity of e g cell wall material with density 0.01–0.03 g/cm$^3$ is during the first minute in the horizontal direction at least 10 mm, preferably 15 mm, more preferably 25 mm, and in the vertical direction at least 5 mm, preferably 10 mm, more preferably 20 mm.

In addition to binding and transportation of liquid the material has high capacity for binding of microorganisms, including bacteria and yeast cells, animal cells macromolecules e g proteins and cell lysis products e g aggregates of molecules and particles. Bovine serum albumin and certain other proteins may be bound at equal weights or more. From a suspension of 100 million *E. coli* cells per ml 80% of the bacteria are bound when 1 mg fungal cell wall material per ml was used.

The cell wall material has a positive zeta-potential at pH 7, and/or a zeta-potential of at least 10 mV at pH 6, preferably at least 20 mV at pH 6, when the cell wall material has been disintegrated into particles less than 20 m. At least 5% (wt/wt) of the cell wall material is hexosamine.

The material can be dried either as it is or bound to one or more surfaces. The surface can be a foam, a film or a fibre e g cellulose or synthetic fibre. Depending on the character of the added surfaces and the quantitative relationships, structures with different binding characteristics can be obtained. The material can also be fastened to a surface after drying. The fungal cell wall material can also be used in hygienic utensils such as incontinence care products, diapers and tampons and in different types of wound care products. Absorbing utensils such as diapers as well as incontinence and feminine care products usually consist of several layers. The fungal cell wall material can be placed directly under a surface material or under an entering/transporting membrane e g a high loft material. In feminine and incontinence care products the cell wall material can be used for absorption and spreading and to prevent malodour. In wound care products the material can be used to bind bacteria and liquids; is it doped with a protein as an enzyme or cytokine new properties can be added.

EXAMPLE

Cultivation of Moulds

Concentrated sulfite liquor (dry wt 50% wt/wt) is diluted with three parts of water. Diammoniumhydrogen phosphate 10 g/l and potassium chloride 1 g/l are added and pH adjusted to 5–7 with sodium hydroxide. The medium may be sterilised at 120° C. and after cooling inoculated with *Rhizopus oryzae* CCUG 28958, mainly as spores. The fungal culture is incubated at 30° C. with agitation and aeration for 48 hrs. Then it is passed over a sieve and washed. The wet weight yield is ca 60–70 g per liter medium (10–20 g dry wt per liter).

Moulds containing chitosan/chitin obtained from the cultivation were disintegrated by freeze-pressing and the protoplasmic content removed by washing in order to produce cell walls. Alternatively the mycelial mass was extracted with an organic solvent e g warm ethanol in order to remove lipids. Then the material was treated with hot sodium hydroxide or enzymes in order to remove proteins and nucleic acids. Acetic acid or lactic acid were used in order to extract soluble chitosan. The method is described more closely in EP 0 494 950 B1 and the Swedish patent application nr. 9801373-3. It is also possible to extract with only sodium hydroxide and acids.

The suspension was freeze-dried with a freeze-dryer provided with a drying chamber and supplied with a vacuum pump and a condenser kept at low temperature. The suspension of cell walls, often gel- or jellylike was spread onto aluminium plates to the desired thickness, ca 3–5 mm, alternatively in polystyrene petri dishes. The plates were put into freezers overnight or for a few days. Then the plates with frozen material was placed into the freeze-drier and exposed to vacuum over-night or for a few days. The material had the same thickness before and after freeze-drying. It was evident that the conditions used for freezing and drying influenced the properties of the dried cell-wall material. The dried material had a very porous structure with densities ca 0.01–0.1 g/cm$^3$. The density of the dried material was a result of the concentration of the cell wall material in the suspension. When e g 10 mg cell wall material per ml liquid was frozen the dried material had a density of 0.01 g/cm$^3$.

Cultivation of moulds with sulfite liquor as a carbon and energy source results in high sugar consumption when suitable strains are used such that lignosulfonate-enriched liquor can be recovered by removal of the fungal mycelium with sieving. In the sieving process certain metabolites of value, e g lactate may also be recovered. When calcium sulfite liquor is used Ca-lactate may appear as long filaments.

In our investigations ca 30 zygomycetes strains representing different species have been cultivated, and great differences between the strains noted with respect to assimilation of different sugars including mannose, galactose, xylose, glucose, and arabinose as well as the capacities of one strain to assimilate the sugars mentioned above. To some extent the assimilation pattern is related to species but differences exist between strains belonging to the same species.

In order to make sulfite liquor useful as cultivation medium for zygomycetes inhibitory substances were removed or neutralised from the original sulfite liquor (dry matter 10%). This can be done by evaporation which eliminates sulfur dioxide and volatile alcohols. However, neither the sulfite liquor (dry matter 10%) nor sulfite liquor concentrated by evaporation (dry matter 50%) will support the growth of zygomycetes but does so after dilution 1:4 (dry matter 12.5%) when sources of nitrogen (e g NH3 or urea) and phosphate are supplied.

When ammonium sulfite liquor is used no extra nitrogen source is needed. Sulfite liquors from different paper mills show very different capacities to support the growth of the zygomycetes tested.

When continuous cultivation is performed less dilution is needed than that used for batch cultures, because the medium is diluted in the culture volume.

The temperature for the cultivation of moulds in media according to the present invention has usually been 28–37° C. However, by the use of thermophilic strains e g of the genus Rhizomucor higher temperatures may be of advantage because of faster growth, less risk of contamination and better heat balance, such that no cooling will be required during the cultivation.

What is claimed is:

1. A process for the elimination of xylose and hexoses from liquid plant material hydrolysates for reduced environmental pollution load of remaining liquid wherein the cultivation of non-toxic zygomycetes fungi with the capacity to assimilate xylose concomitant to the hexoses, whereby the said zygomycetes are harvested by sieving.

2. A process according to claim 1, wherein the cultivation of non-toxic zygomycetes fungi with the capacity to rapidly assimilate xylose concomitant to the hexoses, whereby the said zygomycetes are harvested by sieving and the dissolved metabolites recovered from the cleared liquid.

3. A process according to claim 1, wherein the said zygomycetes mycelial mass is harvested by other means than sieving.

4. A process according to claim 1, wherein the harvested zygomycetes mycelial mass is used for the production of zygomycetes cell wall absorbent material.

5. A process according to claim 1, wherein the harvested mycelial mass is used for the production of chitosan.

6. A process according to claim 1, wherein the harvested mycelial mass is used for the production of omega-3-fatty acids.

7. A process according to claim 1, wherein the harvested mycelial mass is used for the production of cell-bound enzymes.

8. A process according to claim 1, wherein the liquid plant material hydrolysate is paper pulp sulfite liquor.

9. A process according to claim 1, wherein any antimicrobial activity present in the liquid plant material hydrolysates has been eliminated.

10. A process according to claim 1, wherein the liquid plant material hydrolysate contains calcium.

11. A process according to claim 1, wherein the liquid plant material hydrolysate fungal cultivation medium has been supplied with at least one nitrogen and one phosphate source.

12. A process according to claim 2, wherein the metabolite is ethanol.

13. A process according to claim 10, wherein the liquid is a calcium-sulfite liquor.

14. A process according to claim 1, wherein the liquid is concentrated sulfite liquor (dry matter 50%) which has been diluted with water and supplied with at least one nitrogen and one phosphate source.

15. A process according to claim 1, wherein the liquid is concentrated sulfite liquor (dry matter 50%) which has been supplied with at least one nitrogen and one phosphate source and used for continuous cultivation.

16. A process according to claim 1, wherein the liquid is ammonium sulfite paper mill liquor which has been supplied with at least one phosphate source.

17. A process according to claim 1, wherein the sulfite liquor shows a dry matter concentration of at most 20% (wt/wt).

18. A process according to claim 1, wherein the fungus belongs to the species *Rhizopus oryzae,* and is preferable the strain *Rhizopus oryzae* CCUG 28958.

19. A process according to claim 1, wherein the metabolite is lactate.

20. A process according to claim 19, wherein the lactate is recovered as insoluble Ca-lactate.

21. A process according to claim 20, wherein the Ca-lactate is filamentous.

22. A process according to claim 1, wherein the remaining liquid is enriched with respect to lignosulfonate as a consequence of elimination of mannose, xylose, galactose, and glucose, and possibly also arabinose and other low molecular weight carbon compounds.

23. A process according to claim 22, wherein the lignosulfonate is recovered from the foam which is formed when the cultivation medium is aerated.

24. A lignosulfonate-enriched sulfite liquor, wherein mannose, xylose, galactose, and glucose have been removed from the sulfite liquor by cultivation of non-toxix zygomycetes fungi with the capacity to assimilate xylose concomitant to the hexoses.

25. A lignosulfonate-enriched sulfite liquor according to claim 24, wherein mannose, xylose, galactose, glucose, arabinose, and/or other low molecular weight carbon compounds have been removed from the sulfite liquor.

* * * * *